US010576289B2

(12) United States Patent
Alcala et al.

(10) Patent No.: US 10,576,289 B2
(45) Date of Patent: Mar. 3, 2020

(54) POWER AND COMMUNICATION OF NEUROCELL CLUSTERS

(71) Applicant: QUALCOMM Incorporated, San Diego, CA (US)

(72) Inventors: Osvaldo Alcala, Chula Vista, CA (US); Stephen Jay Shellhammer, Ramona, CA (US); William Henry Von Novak, III, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 282 days.

(21) Appl. No.: 15/685,780

(22) Filed: Aug. 24, 2017

(65) Prior Publication Data

US 2018/0236247 A1 Aug. 23, 2018

Related U.S. Application Data

(60) Provisional application No. 62/460,321, filed on Feb. 17, 2017.

(51) Int. Cl.
*A61N 1/372* (2006.01)
*A61N 1/378* (2006.01)
(Continued)

(52) U.S. Cl.
CPC ....... *A61N 1/37229* (2013.01); *A61N 1/3787* (2013.01); *A61N 1/37288* (2013.01);
(Continued)

(58) Field of Classification Search
CPC ........ H01Q 1/2225; H01Q 1/273; H01Q 3/24; H01Q 21/061; H01Q 1/2216; H01Q 1/27;
(Continued)

(56) References Cited

U.S. PATENT DOCUMENTS 8,948,871 B2 2/2015 Mashiach et al.
9,248,302 B2 2/2016 Mashiach et al.
(Continued)

FOREIGN PATENT DOCUMENTS

WO 2010042054 A1 4/2010
WO 2013009371 A1 1/2013
(Continued)

OTHER PUBLICATIONS

International Search Report and Written Opinion—PCT/US2018/013008—ISA/EPO—dated Apr. 3, 2018.

*Primary Examiner* — Christine H Matthews
*Assistant Examiner* — Joshua Daryl D Lannu
(74) *Attorney, Agent, or Firm* — Kilpatrick Townsend & Stockton, LLP

(57) ABSTRACT

Techniques described herein address these and other issues by providing an architecture of antennas capable of generating a relatively even H-field without exceeding exposure limits, while solving communication issues at the same time. More specifically techniques described herein are directed toward the use of multiple antennas that enable an interrogator device of a biological measurement and stimulation system to power different groups of medical implants at different times by creating fields in different regions of the brain. By doing this, the interrogator device can independently power and/or communicate with groups of medical implants in these different regions and create more evenly-distributed fields while doing so.

24 Claims, 11 Drawing Sheets

(51) Int. Cl.
*H01Q 1/27* (2006.01)
*H01Q 1/22* (2006.01)
*H01Q 21/06* (2006.01)
*H01Q 3/24* (2006.01)

(52) U.S. Cl.
CPC ......... *H01Q 1/2216* (2013.01); *H01Q 1/2225* (2013.01); *H01Q 1/27* (2013.01); *H01Q 1/273* (2013.01); *H01Q 3/24* (2013.01); *H01Q 21/061* (2013.01); *A61N 1/37276* (2013.01)

(58) Field of Classification Search
CPC .............. A61N 1/37288; A61N 1/3787; A61N 1/37229
See application file for complete search history.

(56) References Cited

U.S. PATENT DOCUMENTS

| | | |
|---|---|---|
| 9,532,726 B2 | 1/2017 | Kim et al. |
| 9,561,381 B2 | 2/2017 | Rao et al. |
| 9,564,777 B2 | 2/2017 | Yeh et al. |
| 2016/0206890 A1 | 7/2016 | Oron et al. |

FOREIGN PATENT DOCUMENTS

| | | | |
|---|---|---|---|
| WO | 2017004531 A1 | 1/2017 | |
| WO | WO-2017004531 A1 * | 1/2017 | ............... A61B 5/04 |

* cited by examiner

POWER AND COMMUNICATION OF NEUROCELL CLUSTERS

RELATED APPLICATIONS

This application claims the benefit of U.S. Provisional Application No. 62/460,321, filed Feb. 17, 2017, entitled "POWER AND COMMUNICATION OF NEUROCELL CLUSTERS", of which is assigned to the assignee hereof, and incorporated herein in its entirety by reference.

BACKGROUND

A biological measurement and stimulation system comprises an interrogator device, located in, on, or near a patient's head, in communication with many medical implants comprising small wireless probes implanted in the patient's brain. These medical implants can take measurements of and/or stimulate portions of the patient's brain, based on communications received from the interrogator device, which can act as a controller for the medical implants. Further, the medical implants may be powered by the interrogator device (e.g., via a coiled antenna drawing power from communications and/or other signals or fields generated by the interrogator device).

However, where a system has many medical implants (e.g., thousands or more), it may take a long time for the interrogator device to communicate with each of them. Furthermore, architectures in which the interrogator device has only a single antenna may produce an uneven field for powering the medical implants, which can result in medical implants getting too much or too little power. Furthermore, in systems having many medical implants, the length of time needed for the interrogator device to communicate with the medical implants may require the antenna to create a field for a length of time that exceeds relevant exposure limits, which limit the duration the brain can be exposed to such fields.

SUMMARY

Techniques described herein address these and other issues by providing an architecture of antennas capable of generating a relatively even magnetic field (H-field) without exceeding exposure limits, while solving communication issues at the same time. More specifically techniques described herein are directed toward the use of multiple antennas that enable an interrogator device of a biological measurement and stimulation system to power different groups of medical implants at different times by creating fields in different regions of the brain. By doing this, the interrogator device can independently power and/or communicate with groups of medical implants in these different regions and create more evenly-distributed fields while doing so.

An example method of operating an interrogator device having a plurality of antennas to power a plurality of medical implants, according to the description, comprises operating a first group of the plurality of antennas during a first time period to provide power to a first corresponding group of the plurality of medical implants while a second group of the plurality of antennas and a second corresponding group of the plurality of medical implants remain in a different power state, and operating the second group of the plurality of antennas during a second time period to provide power to the second corresponding group of the plurality of medical implants while the first group of the plurality of antennas and the first corresponding group of the plurality of medical implants remain in the different power state.

The method may include one or more of the following features. The antennas in the first group of the plurality of antennas may not be adjacent to each other. The antennas in the first group of the plurality of antennas may be adjacent to each other, and the method may further comprise operating an antenna at a center of the first group of the plurality of antennas with a first current and operating the other antennas of the first group of the plurality of antennas with a second current, the second current being smaller than the first current. All antennas in the first group of the plurality of antennas may produce a field that meets at least a first threshold amplitude at a certain depth. The antenna at the center of the first group of the plurality of antennas may produce a field that meets at least a second threshold amplitude at the certain depth, the second threshold amplitude being higher than the first threshold amplitude. The method may further comprise executing a discovery process to determine which one or more medical implants devices of the plurality of medical implants devices receive power during the first time period.

An example interrogator device, according to the description, comprises a plurality of antennas configured to power a plurality of medical implants, and circuitry communicatively coupled with the plurality of antennas. The circuitry is configured to operate a first group of the plurality of antennas during a first time period to provide power to a first corresponding group of the plurality of medical implants while a second group of the plurality of antennas and a second corresponding group of the plurality of medical implants remain in a different power state, and operate the second group of the plurality of antennas during a second time period to provide power to the second corresponding group of the plurality of medical implants while the first group of the plurality of antennas and the first corresponding group of the plurality of medical implants remain in the different power state.

The interrogator device may comprise one or more the following features. The antennas in the first group of the plurality of antennas may not be adjacent to each other. The antennas in the first group of the plurality of antennas may be adjacent to each other, and the circuitry may be further configured to operate an antenna at a center of the first group of the plurality of antennas with a first current and operate the other antennas of the first group of the plurality of antennas with a second current, the second current being smaller than the first current. All antennas in the first group of the plurality of antennas may be configured to produce a field that meets at least a first threshold amplitude at a certain depth. The antenna at the center of the first group of the plurality of antennas are configured to produce a field that meets at least a second threshold amplitude at the certain depth, the second threshold amplitude being higher than the first threshold amplitude. The circuitry may be further configured to execute a discovery process to determine which one or more medical implants of the plurality of medical implants receive power during the first time period.

An example apparatus, according to the description, comprises means for operating a first group of a plurality of antennas during a first time period to provide power to a first corresponding group of a plurality of medical implants while a second group of the plurality of antennas and a second corresponding group of the plurality of medical implants remain in a different power state, and means for operating the second group of the plurality of antennas during a second time period to provide power to the second corresponding group of the plurality of medical implants while the first group of the plurality of antennas and the first corresponding group of the plurality of medical implants remain in the different power state.

The example apparatus may further comprise one or more the following features. The means for operating the first group of the plurality of antennas may comprise means for selecting the antennas in the first group of the plurality of antennas such that they are not adjacent to each other. The means for operating the first group of the plurality of antennas may comprise means for selecting the antennas in the first group of the plurality of antennas such that they are adjacent to each other, the apparatus further may comprise means for operating an antenna at a center of the first group of the plurality of antennas with a first current and operating the other antennas of the first group of the plurality of antennas with a second current, the second current being smaller than the first current. The means for operating the first group of the plurality of antennas may comprise means for causing all antennas in the first group of the plurality of antennas to produce a field that meets at least a first threshold amplitude at a certain depth. The means for operating the first group of the plurality of antennas may further comprise means for causing the antenna at the center of the first group of the plurality of antennas to produce a field that meets at least a second threshold amplitude at the certain depth, the second threshold amplitude being higher than the first threshold amplitude. The apparatus may further comprise means for executing a discovery process to determine which one or more medical implants of the plurality of medical implants receive power during the first time period.

An example non-transitory computer-readable medium has instructions embedded thereon for operating an interrogator device having a plurality of antennas to power a plurality of medical implants. The instructions comprise computer code for operating a first group of the plurality of antennas during a first time period to provide power to a first corresponding group of the plurality of medical implants while a second group of the plurality of antennas and a second corresponding group of the plurality of medical implants remain in a different power state, and operating the second group of the plurality of antennas during a second time period to provide power to the second corresponding group of the plurality of medical implants while the first group of the plurality of antennas and the first corresponding group of the plurality of medical implants remain in the different power state.

The non-transitory computer-readable medium can include one or more of the following features. The computer code for operating the first group of the plurality of antennas may comprise computer code for selecting the antennas in the first group of the plurality of antennas such that they are not adjacent to each other. The computer code for operating the first group of the plurality of antennas may comprise computer code for selecting the antennas in the first group of the plurality of antennas such that they are adjacent to each other, the instructions may further comprise computer code for operating an antenna at a center of the first group of the plurality of antennas with a first current and operating the other antennas of the first group of the plurality of antennas with a second current, the second current being smaller than the first current. The computer code for operating the first group of the plurality of antennas may comprise computer code for causing all antennas in the first group of the plurality of antennas to produce a field that meets at least a first threshold amplitude at a certain depth. The computer code for operating the first group of the plurality of antennas may further comprise computer code for causing the antenna at the center of the first group of the plurality of antennas to produce a field that meets at least a second threshold amplitude at the certain depth, the second threshold amplitude being higher than the first threshold amplitude. The instructions further may comprise computer code for executing a discovery process to determine which one or more medical implants of the plurality of medical implants receive power during the first time period.

BRIEF DESCRIPTION OF DRAWINGS

Non-limiting and non-exhaustive aspects are described with reference to the following figures, wherein like reference numerals refer to like parts throughout the various figures unless otherwise specified.

DETAILED DESCRIPTION

Several illustrative embodiments will now be described with respect to the accompanying drawings, which form a part hereof. The ensuing description provides embodiment(s) only, and is not intended to limit the scope, applicability or configuration of the disclosure. Rather, the ensuing description of the embodiment(s) will provide those skilled in the art with an enabling description for implementing an embodiment. It is understood that various changes may be made in the function and arrangement of elements without departing from the spirit and scope of this disclosure.

It will be understood by a person of ordinary skill in the art that, although the embodiments provided herein are directed toward medical applications, the techniques described herein may be utilized in other applications involving digital communication. Additionally, embodiments provided herein describe the use of "medical implants," although such implants may be utilized to gather data and/or stimulate a body part without necessarily performing a medical function. A person of ordinary skill in the art will recognize many variations.

Figure 1:
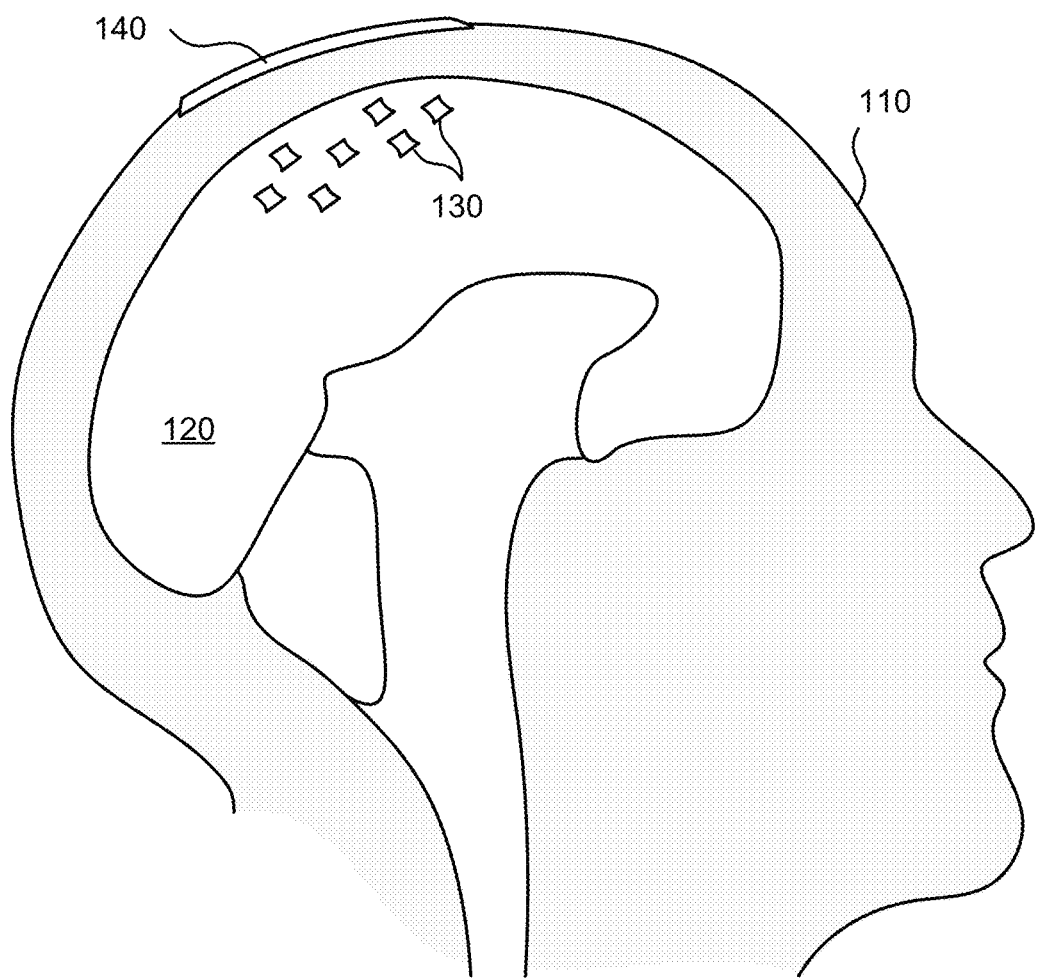
FIG. 1 is a simplified cross-sectional diagram illustrating an embodiment of a biological measurement and stimulation system.

FIG. 1 is a simplified cross-sectional diagram illustrating an embodiment of a biological measurement and stimulation system. Here, a patient's head 110 is illustrated, indicating a portion of the brain 120 in which a plurality of medical implants 130 are implanted. (For clarity, only a portion of the medical implants are labeled.) An interrogator device 140 can comprise one or more devices in communication with the medical implants 130, acting as a central controller for the medical implants 130 and using low-power, short-range radio frequency (RF) signals at a designated frequency communicate with and (in some embodiments) to provide power to the implants. Such wireless communication can employ any of a variety of short-range wireless technologies, including near-field communication (NFC) and/or other wireless technologies. According to some embodiments, data may be communicated in a secure fashion (e.g., using any of a variety of encryption techniques).

For scenarios in which the biological measurement and stimulation system is utilized to measure and stimulate a portion of the brain (as shown in FIG. 1), the interrogator device 140 may be referred to as a "skin patch" because it may be substantially flat in shape and may be disposed on or near the patient's skin. The medical implants 130 in such scenarios may be referred to as "neurograins" because of their relatively small size and location within the patient's brain. That said, although the interrogator device 140 can be located on top or elsewhere attached to the outside the patient's head 110, alternative embodiments many include one or more devices located elsewhere, including in, on and/or in proximity to the patient's body.

Depending on the application, the biological measurement and stimulation system may comprise hundreds or thousands of medical implants 130. (Alternative embodiments may include a smaller or larger number of medical implants 130 than this.) These medical implants 130 can also communicate back to the interrogator device 140 (e.g., through RF backscatter, by changing the impedance of their respective antennas) using a time division multiple access (TDMA) protocol. The interrogator device 140 may coordinate the uplink transmission.

Medical implants 130 can comprise active devices (having a power source) and/or passive devices (having no power source) configured to take biological measurements of the brain 120 (e.g., information regarding electrical signals generated by the patient's brain cells) and communicate the measurements to the interrogator device 140 and/or provide stimulation of the patient's brain 120 (e.g., via one or more electrodes), where such stimulation may be based on communication received from the interrogator device 140. As previously noted, medical implants 130 can be powered by the interrogator device 140 using, for example, a coiled antenna drawing power from communications and/or other signals or fields generated by the interrogator device 140. It can be noted that, in alternative embodiments, the interrogator device 140 may comprise multiple antennas, and/or the biological measurement and stimulation system may have one or more nodes and/or devices between the medical implants 130 and the interrogator device 140. Because medical implants 130 can vary in functionality, they can vary in size, shape, type, and/or may have electrodes (and or other sensors) that vary as well.

Medical implants 130 may draw power from the interrogator device 140 (e.g., via a coiled antenna drawing power from communications and/or other signals or fields generated by the interrogator device 140), and may be passive (e.g., with no independent power source) or active. Active medical implants 130 may also draw power wirelessly from the interrogator device 140, which may be used to charge a battery or other power source(s). As noted below, an interrogator device 140 may comprise multiple antennas and/or the brain biological measurement and stimulation system may have one or more nodes (e.g., modules or devices) between the interrogator device 140 and the medical implants 130.

Figure 11:
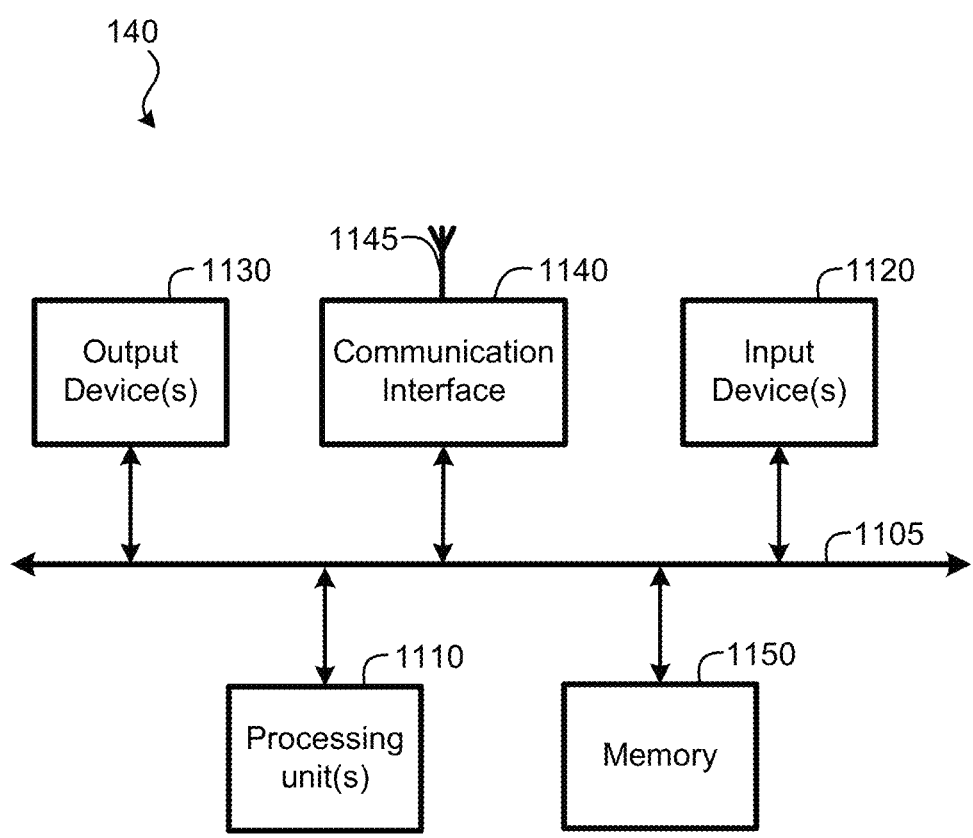
FIG. 11 is a block diagram of a interrogator device, according to an embodiment.
Figure 12:
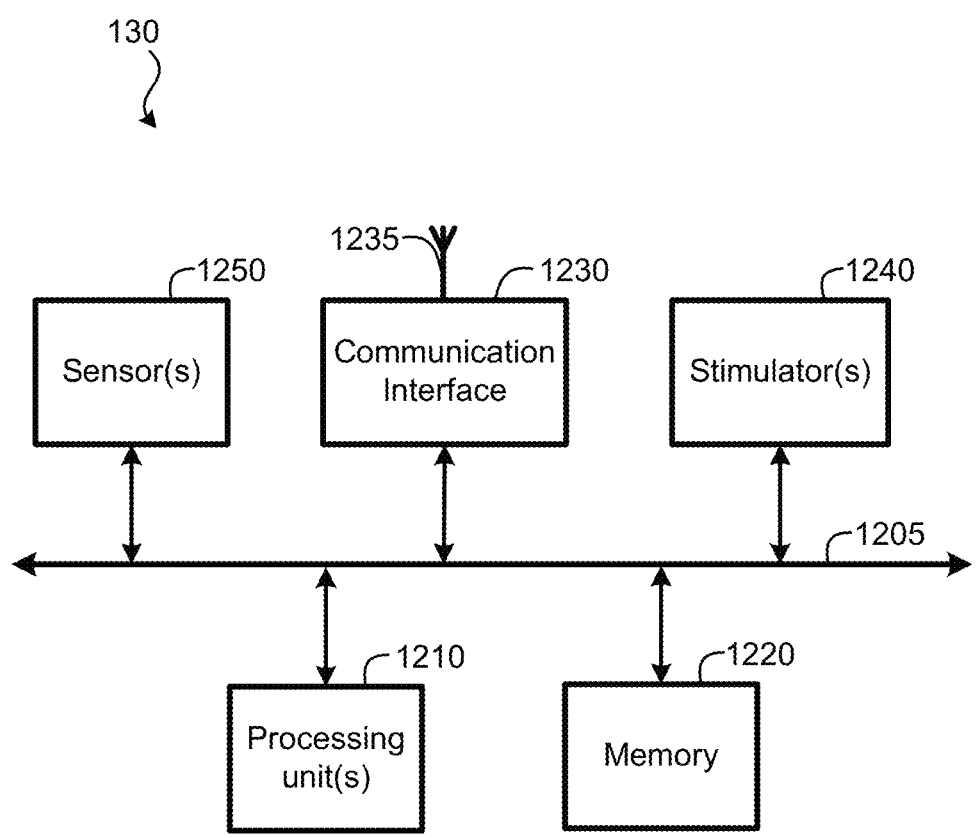
FIG. 12 is a block diagram of a medical implant, according to an embodiment.

A person of ordinary skill in the art will appreciate the basic hardware configuration of an interrogator device 140 and/or medical implant 130. This can include, for example, a power source, processing unit, communication bus, volatile and/or non-volatile memory (which may comprise a non-transitory computer-readable medium having computer code for execution by the processing unit), transceiver, antenna, etc. The medical implant 130 may further comprise one or more sensors, electrodes, and/or stimulators utilized for sensing and/or stimulating one or more parts of the body. As such, the interrogator device 140 and/or medical implant 130 may have means for performing some, or all, of the functions described herein using one or more of its hardware and/or software components. In some embodiments, components may be selected and/or optimized for low power consumption. In particular, because medical implants 130 may be limited in size and/or power, the medical implants 130 may not have the same memory size and/or processing capabilities as the interrogator device 140. Example electrical hardware and software components of an interrogator device 140 and medical implant 130 are illustrated in FIG. 11 and FIG. 12, respectively, and described in more detail below.

For biological measurement and stimulation systems such as the one shown in FIG. 1, an increased number of medical implants 130 in a particular system results in a longer amount of time required for the interrogator device 140 to communicate with each of the medical implants 130. Furthermore, in architectures in which the interrogator device 140 has only a single antenna may produce an uneven field for powering the medical implants 130, which can result in medical implants 130 getting too much or too little power to operate properly. Furthermore, in systems having a large number of medical implants 130, the length of time needed for the interrogator device 140 to communicate with the medical implants 130 may require that the antenna creates a field for a length of time that exceeds relevant exposure limits, which limit the amount of time the brain can be exposed to such fields.

Embodiments provided herein address these and other issues by providing an architecture of antennas capable of generating a relatively even H-field without exceeding exposure limits, while solving communication issues at the same time. More specifically techniques described herein are directed toward the use of multiple antennas that enable an interrogator device of a biological measurement and stimulation system to power different groups of medical implants at different times by creating fields in different regions of the brain. By doing this, the interrogator device can independently power and/or communicate with groups of medical implants in these different regions and create more evenly-distributed fields while doing so.

Figure 2:
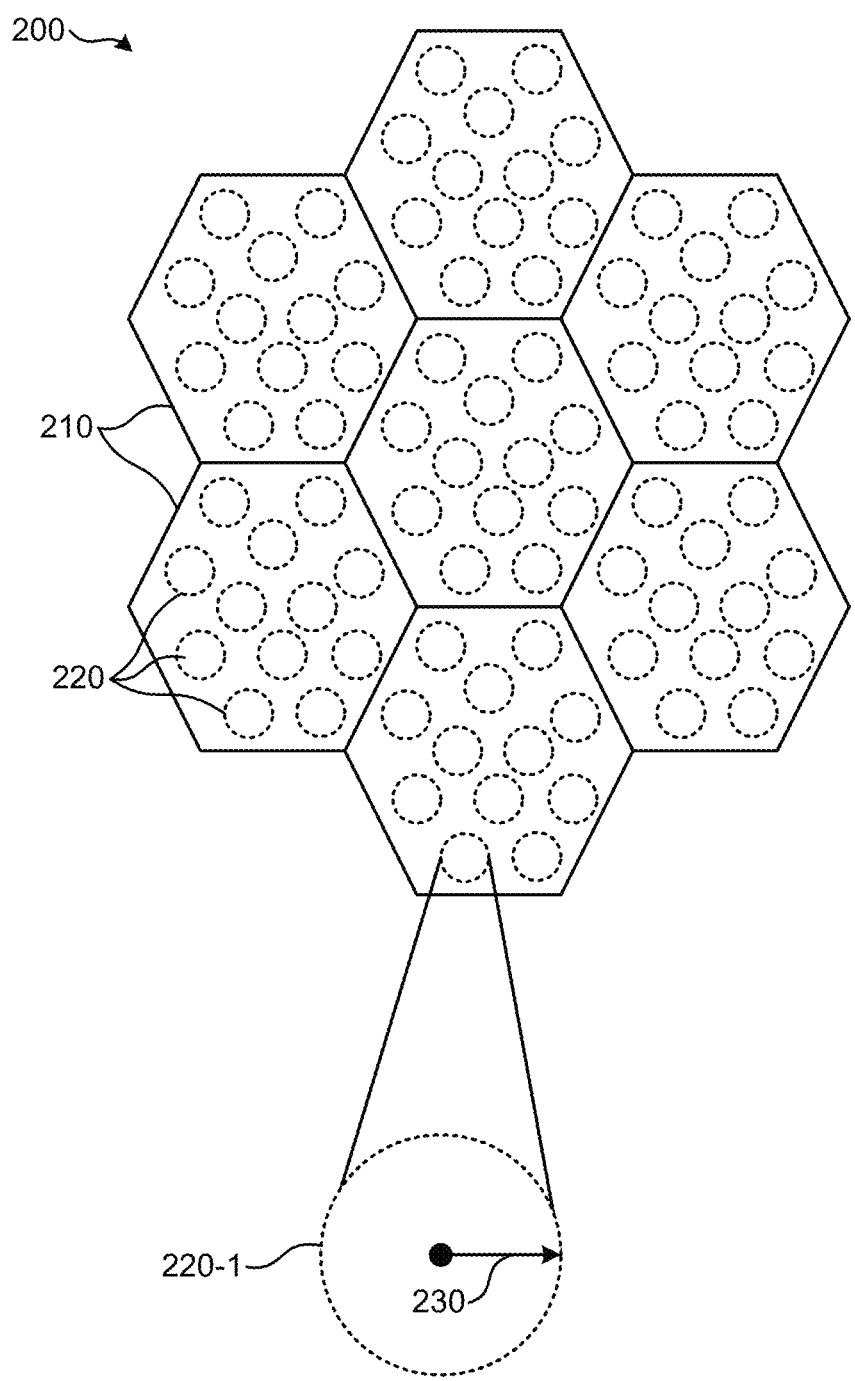
FIG. 2 is a simplified diagram illustrating a cell-based topology of a coverage area of a biological measurement and stimulation system, according to an embodiment.

FIG. 2 is a simplified diagram illustrating the cell-based topology of a coverage area 200 of a biological measurement and stimulation system, according to an embodiment. Here, the coverage area 200 is illustrated as a group of two-dimensional hexagon-shaped cells 210. (To avoid clutter, not all cells are labeled in FIG. 2.) It will be noted, however, that the medical devices may typically be distributed within the brain in a three-dimensional fashion, such that the coverage area 200 of the biological measurement and stimulation system may be considered more of a "coverage volume." Nonetheless, the simplified drawing is utilized for illustrative purposes that help describe the embodiments provided herein.

Here, each cell 210 represents a region of the brain powered by a different antenna of the interrogator device. The seven cells 210 of the coverage area 200 illustrated in FIG. 2 would therefore correspond to a skin patch having seven different antennas (which may be disposed in, on, or near the interrogator device in such a way as to power the medical implants located within the different cells 210). The hexagonal shape of each cell 210 is shaped as such for simplicity in the illustration. In physical embodiments, the cells 210 may take different shapes (including 3-dimensional volumes), which may be based on the type of field generated by the cells' respective antennas, and which may overlap with other cells 210.

Medical implant fields 220 are illustrated as circles within each cell 210. Each medical implant field 220 corresponds to a medical implant 130, and represents the field produced by a medical implant during uplink communication with the interrogator device. The circle near the bottom of FIG. 2 is a close-up view of a medical implant field 220-1 with a given radius 230. It can be noted that, although each medical implant field 220 is illustrated as having the same or similar radius, actual coverage areas/volumes of medical implant fields 220 may take different sizes, shapes, and/or volumes. Furthermore, in any given implementation the number of medical implants (and consequently medical implant fields 220) can vary from cell to cell, depending on medical implant density, cell size/volume, and/or other factors.

It can be noted that in some embodiments, for each cell 210, the interrogator device may use a single antenna to power and communicate (transmit and receive) with medical implants for that cell 210. In some embodiments, multiple antennas may be used, where different antennas are used for different functions.

Figure 3:
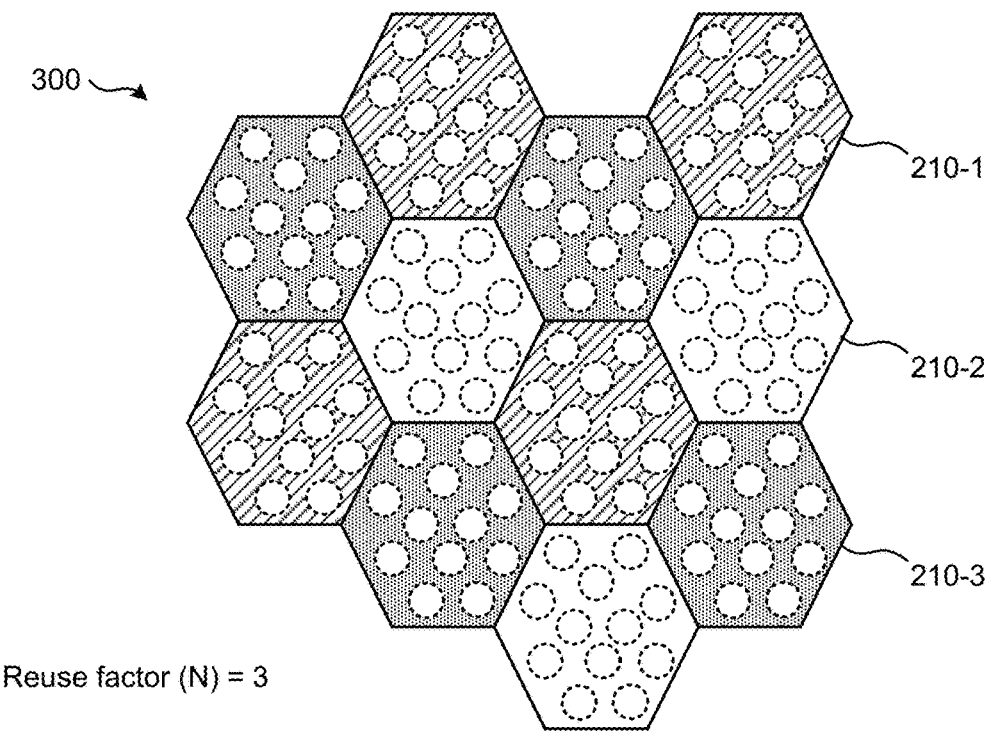
FIG. 3 is a simplified diagram the topology of a coverage area of a biological measurement and stimulation system, illustrating how power and communication may be managed within a cell-based architecture (similar to FIG. 2), according to embodiments.

FIG. 3 is a simplified diagram the topology of a coverage area 300 of a biological measurement and stimulation system, illustrating how power and communication may be managed within a cell-based architecture (similar to FIG. 2), according to embodiments. Here, the coverage area 300 has 11 different cells 210, split into three different groups (or clusters): a first group 210-1, a second group 210-2, and a third group 210-3. (In the illustration, only a single cell of each group is labeled, but all similarly-shaded cells belong to a single group. Thus, the first group 210-1 comprises four cells, the second group 210-2 comprises three cells, and the first group 210-3 comprises four cells.)

Here, the "reuse factor (N)" is reflective of a duty cycle in which each of these cells are powered, which reflects the number of groups in the coverage area 300. Thus, the reuse factor (N) of coverage area 300 is three. This means that the interrogator device powers all medical implants within cells 210 of a single group (e.g., the first group 210-1) at a time, cycling from one group to the next, such that the medical implants of each group of cells is powered approximately ⅓ of the time. (It can be noted, however, that in some embodiments and/or scenarios, there may be times during which no cells are powered. It can also be noted that cell groups do not necessarily have to be mutually exclusive. Thus a single cell may be part of two different groups for example, which may impact the reuse factor and duty cycle.)

Figure 4:
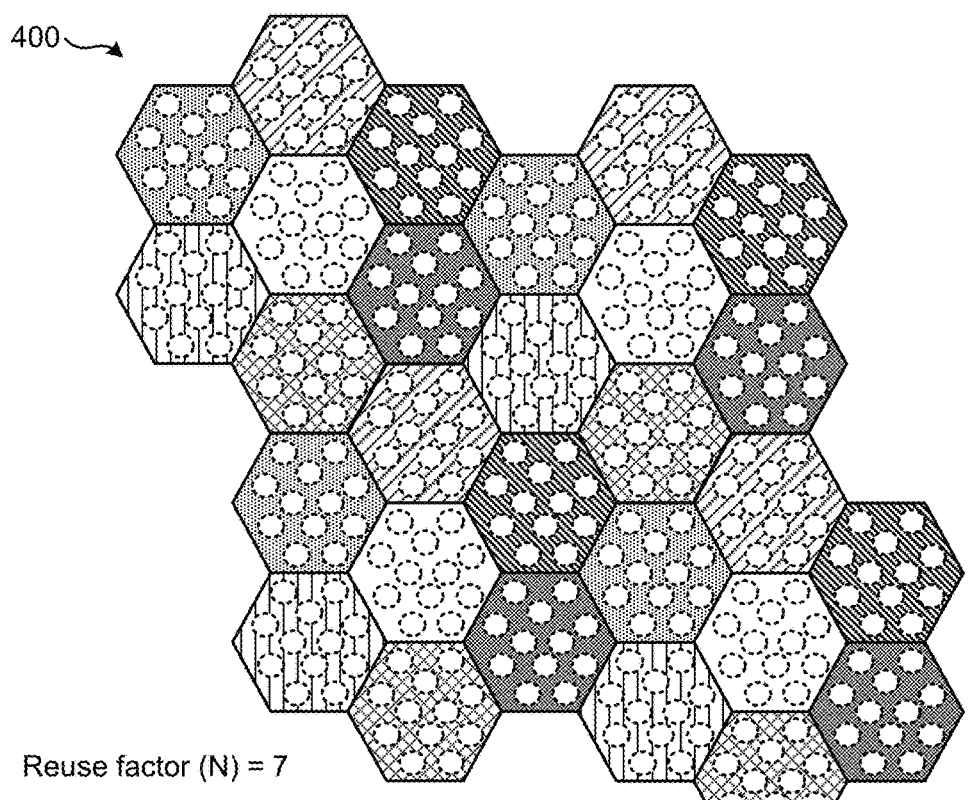
FIG. 4 is a diagram of an embodiment of yet another coverage area.

FIG. 4 is a diagram of an embodiment of yet another coverage area 400. Here, cells (not labeled in FIG. 4) of the coverage area 400 are divided into seven different groups, rather than three. (Again, different shades of cells represent different groups.) As such the reuse factor is seven, and the medical implants of each group of cells is powered approximately ⅐ of the time. Accordingly, using this cell-based architecture can result in a reduced amount of exposure for each region of the brain covered by each cell, while still enabling the interrogator device to communicate with each medical implant in its coverage area 400.

As illustrated in FIGS. 3 and 4, groups of cells may be interspersed so that cells of a particular group are not adjacent. This can help reduce the likelihood of interference and/or field cancellation in certain circumstances. (More on this below.) However, alternative embodiments may range cells in different fashions to achieve different functionality. Examples of such alternative embodiments are illustrated in FIGS. 7 and 8, which are described in more detail below.

Communication may be handled differently, depending on desired functionality. For example, in some embodiments, a TDMA schedule may cover all medical implants in a group of cells. For example, if there are four cells in a group, and 10 medical implants in each cell, a TDMA schedule may have 40 time slots, one for each medical implant in the entire group of cells. In this case, although four different antennas of the interrogator device may be used to power the medical implants of all four cells at once, there may only need to be one set of communication circuitry coupled to those four antennas to enable communication medical implants in the group. In some embodiments, however, the interrogator device may be able to communicate simultaneously with cells within a group. That is, if four cells of a group are powered on simultaneously, the interrogator device may include a different set of communication circuitry coupled to each of the antennas powering cells of the group. This can result in each cell having its own TDMA schedule, vastly increasing the capacity (or amount of medical implants with which the interrogator device may communicate). For embodiments configured to enable simultaneous communication in this manner, the different cells of a group of cells may be distributed in a manner similar to that which is shown in FIGS. 3 and 4 such that there is one or more cells between two cells of the same group. This can help minimize the likelihood of interference during communication.

The number of antennas of an interrogator device can be determined based on any of a variety of pertinent factors. Such factors include, without limitation, exposure limits (limiting the amount of time a region of the brain (or other tissue) is exposed to an electromagnetic field), a desired duty cycle or reuse factor, communication speed (the faster things are communicated, the shorter time as needed to do so), a desired minimum distance between cells of the same group (to reduce interference), and so forth. With regard to the duty cycle/reuse factor, there may be a minimum amount of time the medical implants may need to be powered to function properly. That said, as illustrated in the embodiments below, there may be ways to power medical implant during periods in which these medical implant are not communicating with the interrogator device.

It is noted that, although the illustrations of FIGS. 2-4 (and similar coverage areas in other figures) clearly demark the boundary between adjacent cells, there may be instances in which a single medical implant may be powered by (i.e., fall within the "coverage area" of) more than one antenna of the interrogator device, and may therefore potentially be grouped into one or more respective cells. To help determine which medical implants belong to which cell, the interrogator device may engage in a medical implant discovery process. This process may be run even if the interrogator device was placed on the patient's head previously, because the placement on the patent's head is likely to be shifted (if only slightly) relative to the previous time.

Figure 5:
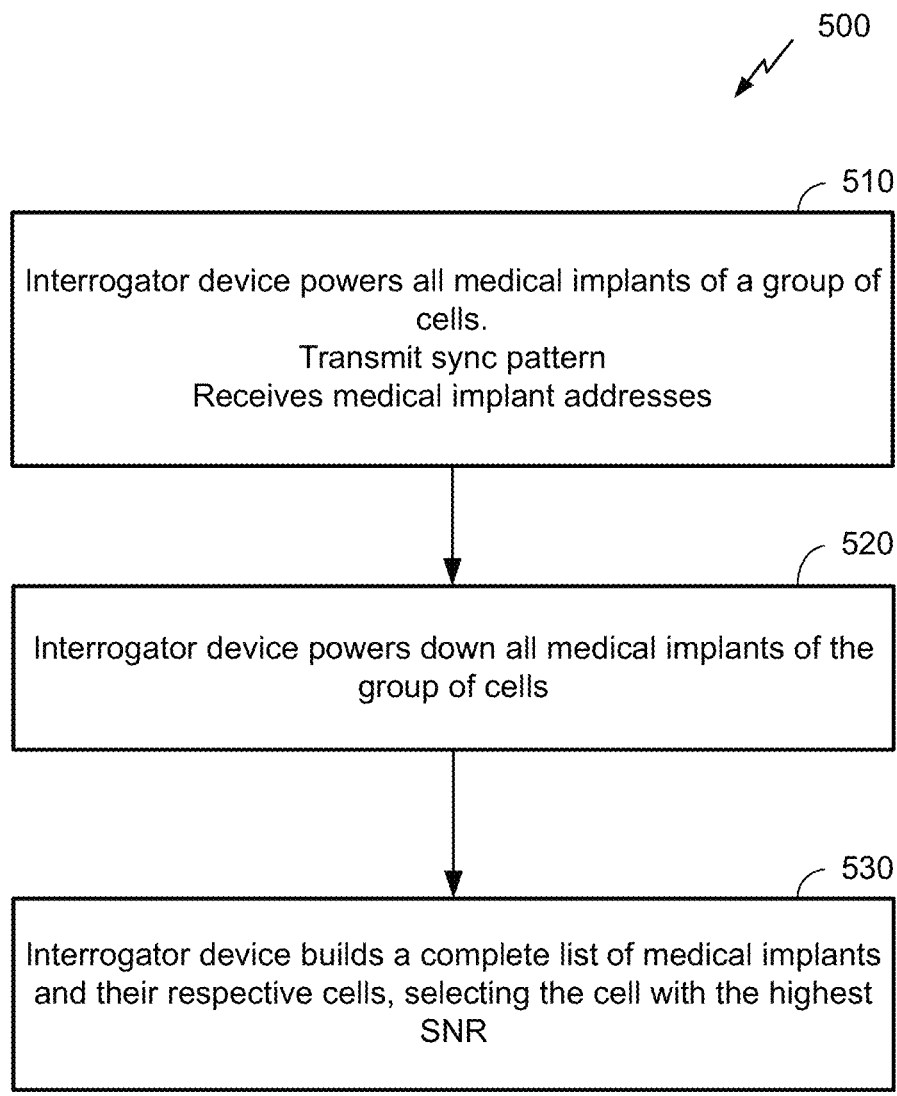
FIG. 5 is a process flow diagram illustrating a method of assigning medical implants to cells, according to an embodiment.

FIG. 5 is a process flow diagram illustrating a method 500 of assigning medical implants to cells, according to an embodiment. It will be understood, however, that embodiments may employ alternative methods that may add, subtract, combine, separate, or otherwise very the functions illustrated in the method 500.

The method 500 can begin with the functionality illustrated in block 510, where the interrogator device powers all medical implants of a group of cells (e.g., the first group 210-1 of FIG. 3. In some embodiments, this can mean that the interrogator device can transmit a synchronization pattern periodically using RF power (e.g., every 100 ms). Each medical implant that is powered up from the RF power it receives may transmit its address to the interrogator device. Because the interrogator device does not know yet which medical implants are powered up, it may not schedule any transmissions from the medical implants. Accordingly, a slotted Aloha protocol (or similar) may be used, where after the synchronization signal, the time afterwards is divided into time slots of predefined duration. These slot durations may be long enough to accommodate a communication packet from a medical implant to the interrogator device carrying the medical implant address, and other necessary fields like a cyclic redundancy check (CRC). For example, if there were N such time slots, each medical implant can randomly pick a number K between 0 and (N−1), to know which time slot to use. Each medical implant can also generate a random number X of either 0 or 1, where the probably of a 1 is p and the probability of a 0 is (1−p). The choice of p is a design parameter selected in advance, based on the number of medical implants and the number of cells. The number p can be relatively high if there are relatively few medical implants, and relatively low if there are relatively many medical implants, per cell.

After the synchronization signal is transmitted, the medical implant checks the value X. If it is 1, then the medical implant can then transmit its address in a packet during time slot K. Each medical implant can continue after each synchronization until the interrogator device sends a message for the medical implant to stop. (There are many ways the interrogator device can send such a stop message.) The interrogator device can keep a list of the addresses it receives and a measure of the signal-to-noise (SNR) for each of those receptions.

At block 520, the interrogator device can, after it has completed a sufficient number of cycles of the synchronization signal (sometimes called a Frame), it power down all medical implants of the group of cells. The interrogator device can then move on to the next group of cells, repeating a similar process for each group.

At block 530, after completing all the groups of cells, the interrogator device can build a complete list of medical implants and their respective cells. Here, if a particular medical implant is covered by multiple cells, the interrogator device can select the cell in which the medical implant had the highest SNR.

Thus, by implementing the functions of the method 500, the interrogator device can end up with a complete list of medical implants for each cell, with each medical implant listed in only one cell's list.

Providing power to the medical implants may be handed differently by different interrogator devices, depending on desired functionality. As previously noted, relatively large single antennas may distribute a field unevenly among the medical implants. For example, a large coil would tend to emit radiation in a hoop shape with a dead spot (having little or no power) in the center. Thus, with a large coil, it would be difficult to adequately power some medical implants without providing too much or too little power to other medical implants.

Figure 6A:
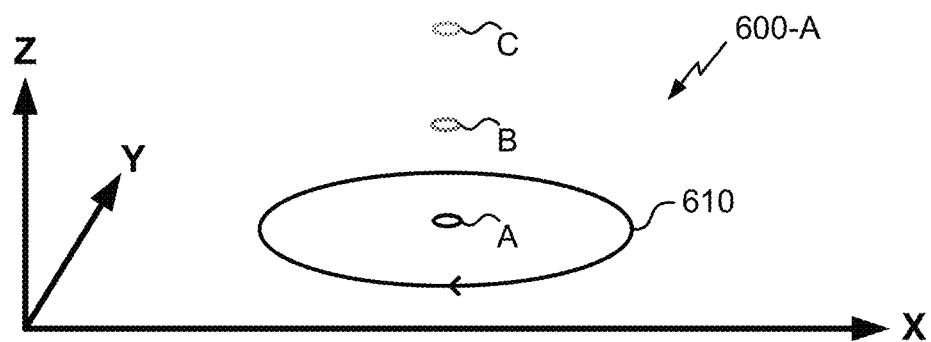
FIGS. 6A-6C are a series of illustrating how field shaping for such applications may be approached in various embodiments.
Figure 6B:
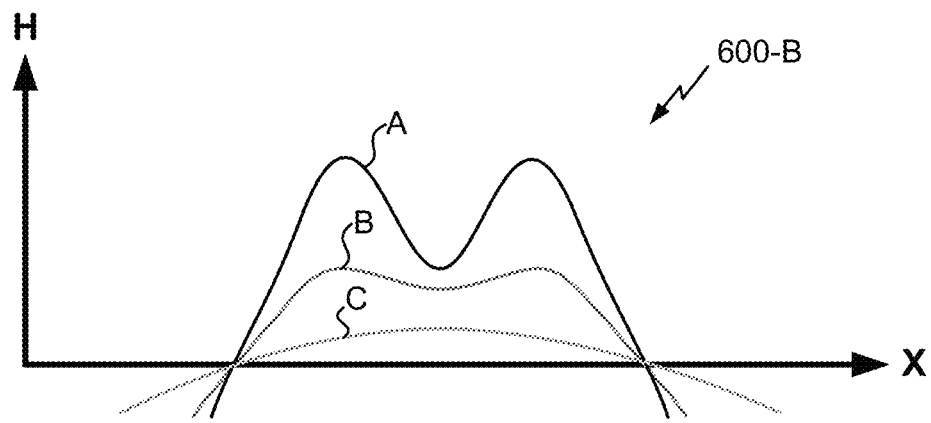
Figure 6C:
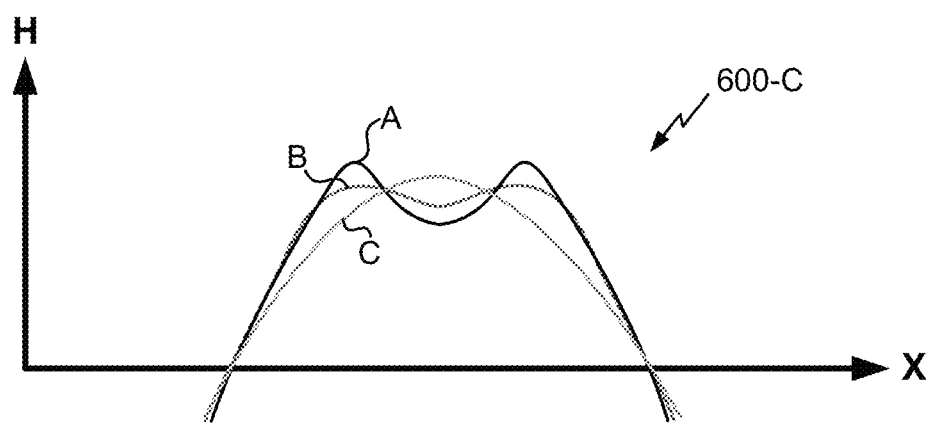

FIGS. 6A-6C are a series of graphs (600-A, 600-B, and 600-C, collectively referred to as graphs 600) illustrating how field shaping for such applications may be approached in various embodiments.

FIG. 6A illustrates a setup in which a transmitting coil 610 (or antenna) is in an XY plane, and much smaller receiving coils (antennas) are located at different distances from the transmitting coil 610, measured in terms of the diameter, D, of the transmitting coil 610. A first receiving coil A is located at a distance of 0D (in the XY plane, at 0% of diameter D), a second receiving coil B is located at 0.5D (50% of diameter D), and a third receiving coil C is located at 1D (100% of the diameter). Here, the transmitting coil 610 can be representative of an antenna of the interrogator device, and the receiving coils A, B, and C, can be representative of antennas embedded within medical implants. FIGS. 6B and 6C illustrate how the different receiving coils A, B, and C will sense an H-field of a transmitting coil antenna 610 differently.

FIG. 6B is an illustration of a graph 600-B, plotting the amplitude of the H field for each of the different receiving coils A, B, and C (of FIG. 6A) as a function of position X. As can be seen, the amount of H-field sensed by the receiving coil A (at 0D) varies along the X axis in a manner that produces two large peaks (see plot A). As distance increases, these peaks are reduced, but so is the overall H field (see plots B and C). A balance can be achieved by increasing a current in the transmitting coil antenna to produce a relatively even H field across the X axis, which may be informed by a knowledge of the distance of the receiving antenna(s) involved. Additional details are included in FIG. 7

Figure 7A:
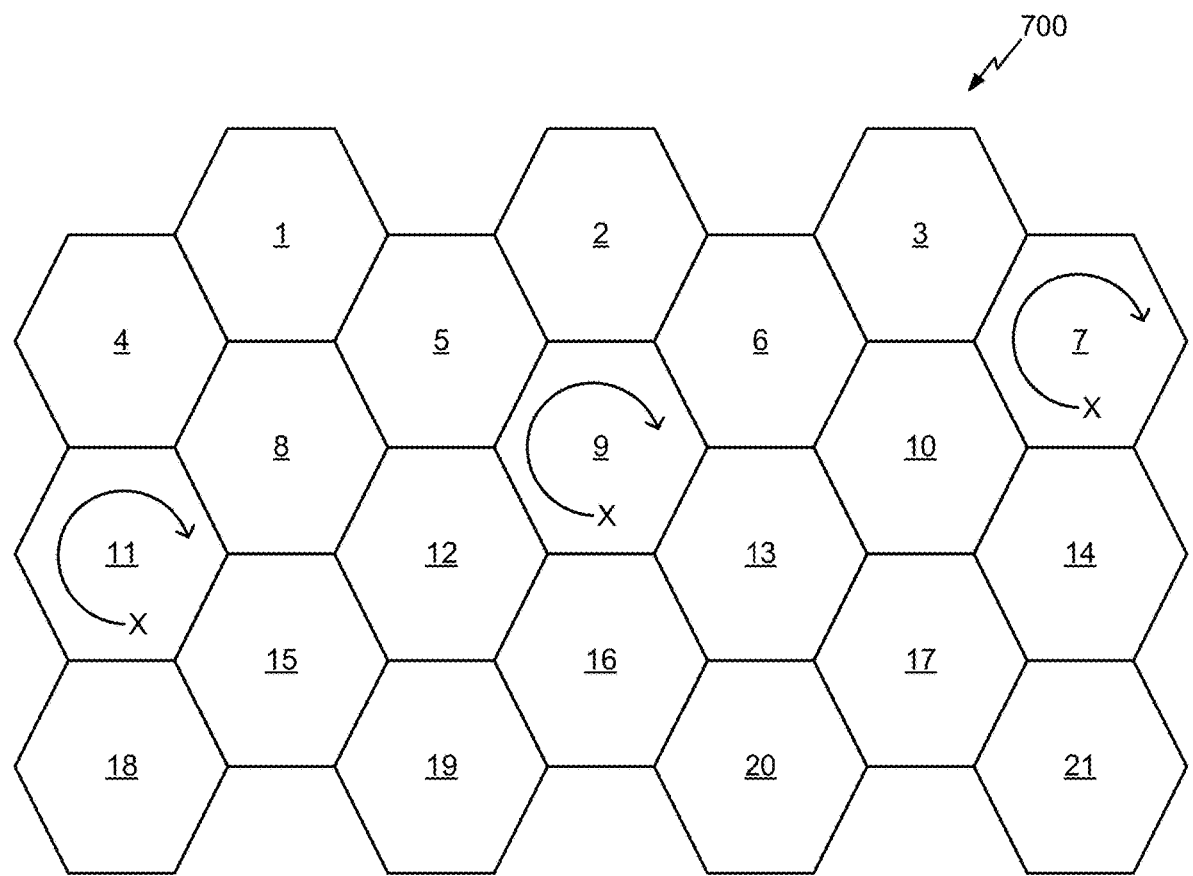
FIGS. 7A and 7B illustrate of a coverage area and corresponding H-field plot, respectively, according to a first embodiment.

FIG. 6C is an illustration of a graph 600-C, again plotting the amplitude of the H field for each of the different receiving coils A, B, and C as a function of position X (similar to graph 600-B). Here, however, it shows a balance in amplitude be achieved by increasing a current in the transmitting coil antenna to produce a relatively even H field across the X axis, which may be informed by a knowledge of the distance of the receiving coils involved. Examples of such a balance are shown in FIGS. 7A-9B and described below FIG. 7A is an illustration of a coverage area 700 showing how different cells may be powered, according to a first embodiment. Here, and interrogator device comprises (or is otherwise couple to) 21 different antennas powering 21 different cells. The size of the antennas may be selected, for example, according to the principles illustrated in FIGS.

6A-6C, to enable each antenna to provide a relatively even field to adequately power all of the medical implants in the respective cell.

Figure 7B:
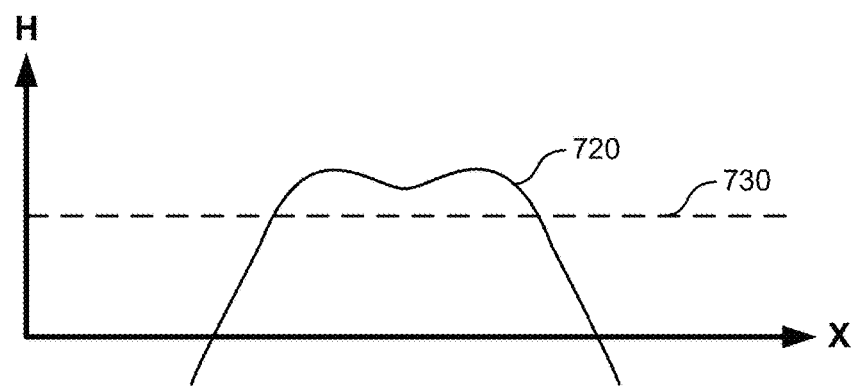

FIG. 7B is a plot 720 of the amplitude of the H-field at a given depth (an average depth of medical implants within a given cell), for the activated cells illustrated in FIG. 7A. Here, the field will power medical implants that receive an H-field that surpasses an operational threshold 730. Thus, given an understanding of the average depth of medical implants within a cell, the corresponding antenna for the cell can be powered to optimize the power and coverage of the H-field.

In some embodiments, the antennas in the interrogator device may overlap to help ensure complete coverage of the "coverage area" of the interrogator device. In the embodiment illustrated in FIG. 7A, three cells are powered at a time. (With 21 cells, the cells may be split into seven groups, or a reuse factor (N) of seven). Field cancellation may occur where two adjacent cells are powered at the same time. Therefore, the cells in each group can be spaced apart to help minimize interference when powered.

Figure 8A:
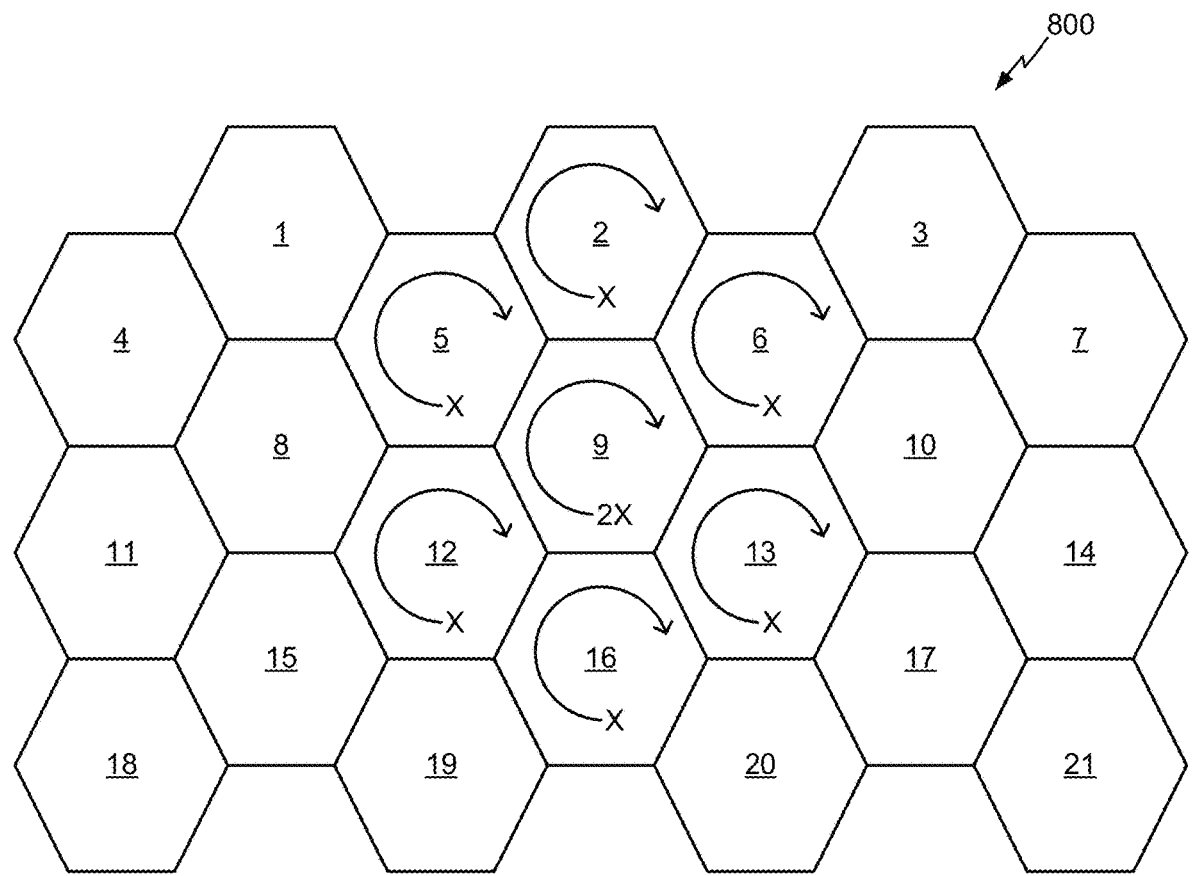
FIGS. 8A and 8B illustrate of a coverage area and corresponding H-field plot, respectively, according to a second embodiment.

FIG. 8A is an illustration of a coverage area 800 showing how different cells may be powered, according to a second embodiment. Here, seven cells (cells 2, 5, 6, 9, 12, 13, and 16) are powered at the same time. Because the coverage area 800 has 21 cells, there may be three mutually exclusive groups in which case there would be a reuse factor (N) of three. This may be helpful in instances where a lower reuse factor is desirable (e.g., where medical implants might need to be powered on a minimum amount of time to operate properly). Here, the group of powered cells are adjacent to one another. However, to compensate for the coverage hole that would otherwise appear in the center of the group of powered cells at cell 9, the antenna corresponding to cell 9 is powered with twice the current (e.g., 2X rather than X).

Figure 8B:
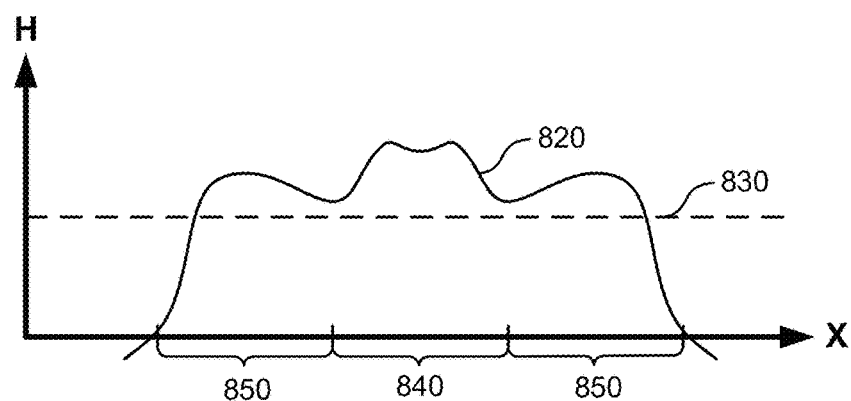

FIG. 8B is a plot 820 of the amplitude of the H-field generated by the group of powered cells at a given depth. An operating threshold 830 is indicated by a dotted line. A center region 840 generally corresponds with a region under the center cell (cell 9), and the side regions 850 generally correspond with regions under the surrounding cells (cells 2, 5, 6, 12, 13, and 16). As noted above, due to field cancellation, the H-field in the center region 840 would fall below the operating threshold 830 of the medical implants if the center cell were driven with as much current as the surrounding cells. But because the center cell is provided with twice as much current, the H-field in the center region 840 remains above the operating threshold 830 for all medical implants in the center region 840 at the depth for which the plot 820 is plotted.

Figure 9A:
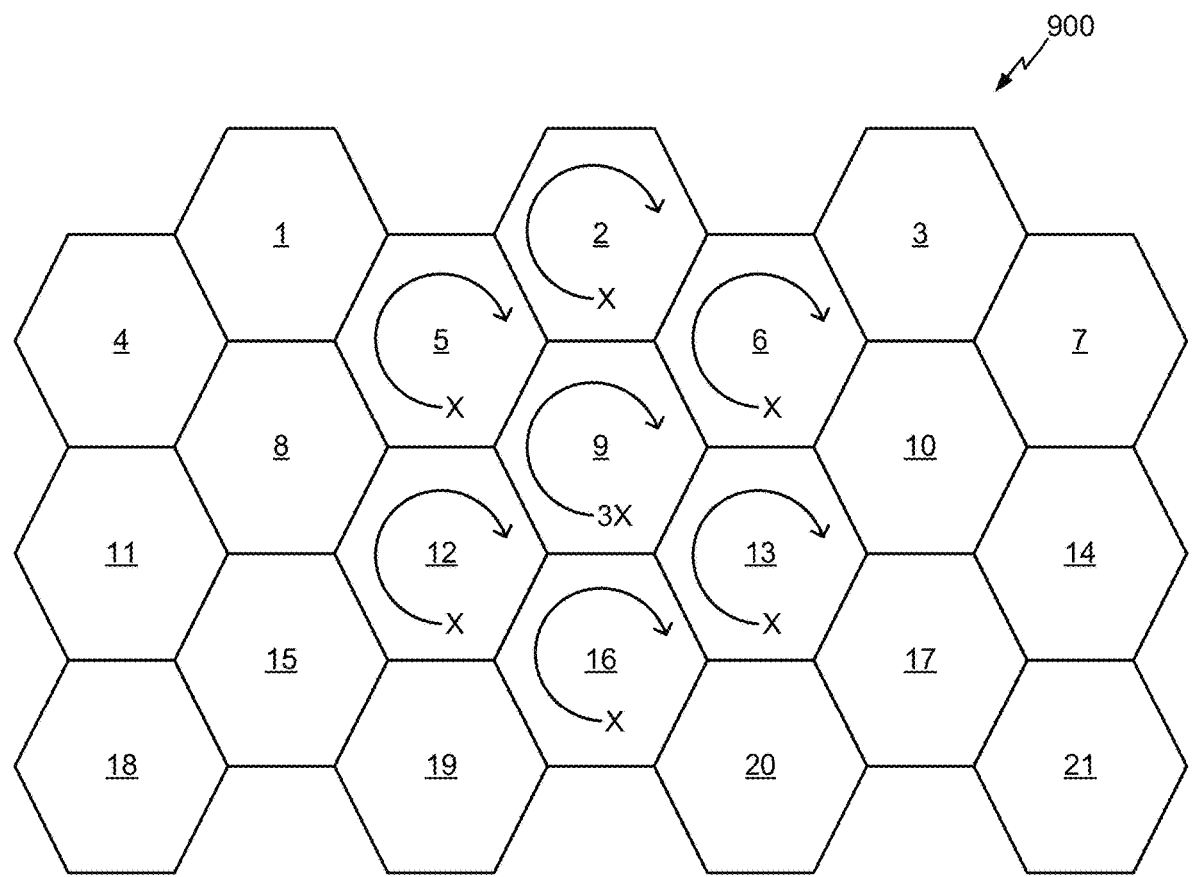
FIGS. 9A and 9B illustrate of a coverage area and corresponding H-field plot, respectively, according to a third embodiment.
Figure 9B:
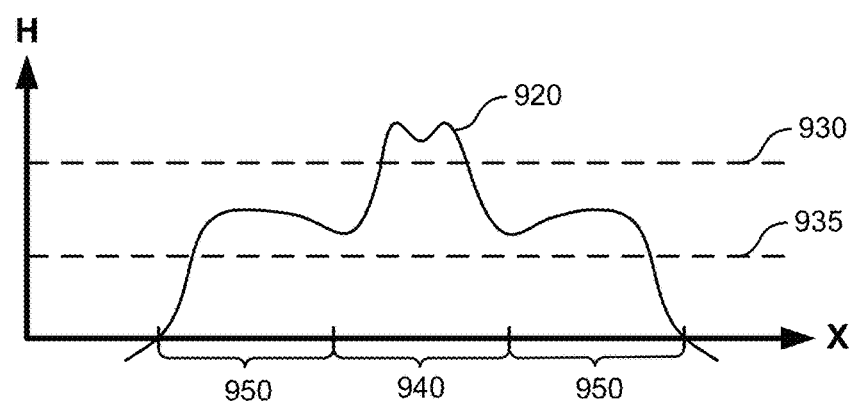

FIGS. 9A and 9B illustrate of a coverage area 900 and corresponding H-field plot 920, respectively, according to a third embodiment. Similar to the embodiment illustrated in FIGS. 8A and 8B, FIGS. 9A and 9B correspond to a group of powered cells with a center cell receiving more current than surrounding cells. However, rather than powering the antenna of the center cell (cell 9) in a manner that simply compensates for the coverage hole in the center region 940 of the group of powered cells (e.g., by using 2X current), the antenna of the center cell is given and even higher current (e.g., 3X) to produce an even stronger H-field in the center cell then in surrounding regions 950. Such functionality may be helpful in scenarios in which there are two different thresholds. That is, there may be an upper threshold 930 at which the medical implants are capable of communicating with the interrogator device and/or performing functions that use a relatively large amount more power, and there may be a lower threshold 935 at which the medical implants are capable of collecting data, operating without communicating to the interrogator device, and/or performing other functions that use a relatively small amount of power. Powering cells in this manner enables the interrogator device to communicate with each cell individually, but also enables the interrogator device to power groups of cells at a time, which may be desirable for adequate function (e.g., data collection brain stimulation, data processing, etc.) of the medical implants.

Figure 10:
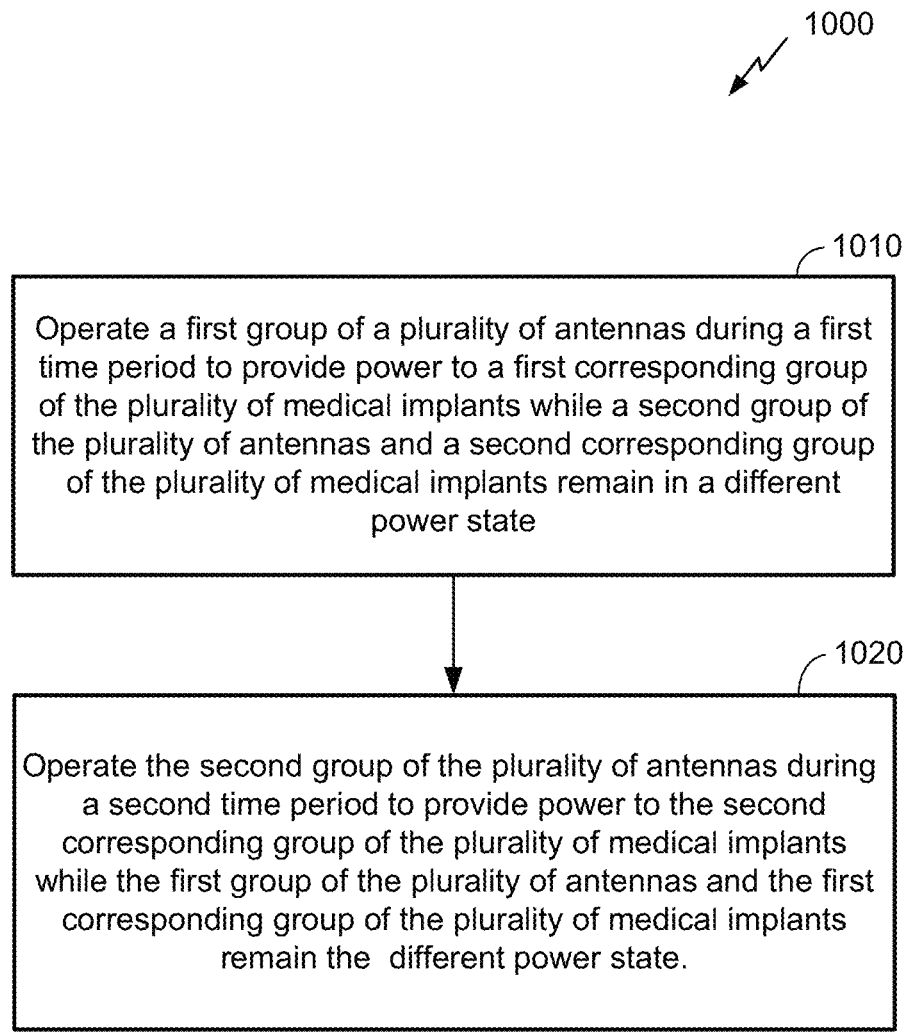
FIG. 10 is a flow diagram of a method of operating an interrogator device having a plurality of antennas to power a plurality of medical implants, according to an embodiment.

FIG. 10 is a flow diagram of a method 1000 of operating an interrogator device having a plurality of antennas to power a plurality of medical implants, according to an embodiment. It will be understood that the method can be implemented by the interrogator device, and the functionality of each of the blocks illustrated in FIG. 10 may be provided by one or more software and/or hardware components of an interrogator device, such as the interrogator device 140 illustrated in FIG. 11 and described in more detail below.

The functionality at block 1010 comprises operating a first group of a plurality of antennas during a first time period to provide power to a first corresponding group of the plurality of medical implants while a second group of the plurality of antennas and a second corresponding group of the plurality of medical implants remain in a different power state. As previously described, antennas of an interrogator device may be grouped together such that one group may power a corresponding plurality of medical implants while another group remains powered off, or two groups of antennas may drive medical implants at different power levels. Means for performing the functionality at block 1010 can processing unit(s) 1110, memory 1150, bus 1105, communication interface 1140, antenna(s) 1145, and/or other components of an interrogator device 140 as illustrated in FIG. 11 and described in more detail below.

At block 1020, the functionality comprises operating the second group of the plurality of antennas during a second time period to provide power to the second corresponding group of the plurality of medical implants while the first group of the plurality of antennas and the first corresponding group of the plurality of medical implants remain in the different power state. Here, the power states switch during a second time period so that the first group of the plurality of medical implants remain in the different power state. Means for performing the functionality at block 1020 can processing unit(s) 1110, memory 1150, bus 1105, communication interface 1140, antenna(s) 1145, and/or other components of an interrogator device 140 as illustrated in FIG. 11 and described in more detail below.

Functionality can vary from the method 1000 illustrated in FIG. 10, depending on desired functionality. For example, in some embodiments, the antennas in the first group of the plurality of antennas may not be adjacent to each other. In some embodiments, as illustrated in FIGS. 8A and 9A, the antennas in the first group of the plurality of antennas may be adjacent to each other, and the method can comprise operating an antenna at the center of the group of the plurality of antennas with a first current and operating the other antennas of the group of the plurality of antennas with a second current, where the second current is smaller than the first current. Moreover, all antennas in the first group of the plurality of antennas may produce a field that meets at least a first threshold amplitude at a certain depth. Optionally, the antenna at the center of the first group of the plurality of antennas may produce a field that meets at least a second threshold amplitude at a certain depth, where the second threshold amplitude is higher than the first threshold amplitude. In some embodiments, a discovery process may be executed to determine which one or more medical devices of the plurality of medical devices receive power during the first time period.

FIG. 11 is a simplified block diagram of a interrogator device 140, according to an embodiment. The interrogator device 140 may comprise a "skin patch" (similar to the interrogator device of FIG. 1) or other device configured to perform one or more of the functions of an interrogator device of a biological measurement and stimulation system as described in embodiments herein. FIG. 11 is meant only to provide a generalized illustration of various components, any or all of which may be included or omitted as appropriate. The interrogator device 140 may be configured to execute one or more functions of the methods described herein, such as the methods corresponding to the functionality described in relation to FIG. 10. It can be further noted that the interrogator device 140 may be configured to receive measurements from and/or stimulate a body part utilizing one or more medical implants with which the interrogator device 140 is in wireless communication, as described in the embodiments above. In some embodiments, the particular measurements taken and/or stimulations may be determined by the interrogator device 140 itself, and/or be determined by another device (such as a medical device, mobile phone, tablet, etc.) with which the interrogator device 140 is in communication. A person of ordinary skill in the art will understand that, for the sake of simplicity, some components (e.g., power source, physical housing, etc.) are not shown.

The interrogator device 140 is shown comprising hardware elements that can be electrically coupled via a bus 1105 (or may otherwise be in communication, as appropriate). The hardware elements may include a processing unit(s) 1110 which may comprise without limitation one or more general-purpose processors, one or more special-purpose processors (such as digital signal processing (DSP) chips, graphics acceleration processors, application specific integrated circuits (ASICs), and/or the like), and/or other logic, processing structure, or means, which can be configured to perform one or more of the methods described herein.

Depending on desired functionality, the interrogator device 140 also may comprise one or more input devices 1120, which may comprise without limitation one or more, touch sensors, buttons, switches, and/or more sophisticated input components, which may provide for user input, which may enable the system to power on, configure operation settings, and/or the like. Output device(s) 1130 may comprise, without limitation, light emitting diode (LED)s, speakers, and/or more sophisticated output components, which may enable feedback to a user, such as an indication the implant system has been powered on, is in a particular state, is running low on power, and/or the like.

The interrogator device 140 might also include a communication interface 1140 and one or more antennas 1145. This communication interface 1140 and antenna(s) 1145 can enable the interrogator device 140 to communicate with and optionally power the medical implants of the biological measurement and stimulation system in the manner described above. The one or more antennas 1145 can be configured to, when power properly, generate particular signals and/or fields to communicate with and/or power the medical implants, including communicating medical implant selection methods as described herein. As previously indicated, medical implants in some embodiments may communicate using RF backscatter, in which case the interrogator device 140 may transmit an RF carrier signal, modulated by the medical implants during uplink communications.

The communication interface 1140 may further enable the interrogator device 140 to communicate with one or more devices outside the biological measurement and stimulation system to which the interrogator device 140 belongs, such as a medical device, mobile phone, tablet, etc. In some embodiments, the one or more devices may execute a software application that provides a user interface (e.g., a graphical user interface) for configuring and/or managing the operation of the interrogator device 140 and/or medical implants. The communication interface may include connectors and/or other components for wired communications (e.g., universal serial bus (USB) Ethernet, optical, and/or other communication). Additionally or alternatively, the communication interface 1140 and optionally the antenna(s) 1145 may be configured to provide wireless communications (e.g., via Bluetooth, Bluetooth low energy, Institute of Electrical and Electronics Engineers (IEEE) 802.11, IEEE 802.15.4 (or ZIGBEE), WIFI, WiMAX, cellular communications, infrared, etc.). As such, the communication interface 1140 may comprise without limitation a modem, a network card, an infrared communication device, a wireless communication device, and/or a chipset.

The interrogator device 140 may further include and/or be in communication with a memory 1150. The memory 1150 may comprise, without limitation, local and/or network accessible storage such as optical, magnetic, solid-state storage (e.g., random access memory ("RAM") and/or a read-only memory ("ROM")), or any other medium from which a computer can read instructions and/or code. The memory 1150 may therefore make the interrogator device 140 can be programmable, flash-updateable, and/or the like. Such storage devices may be configured to implement any appropriate data stores, including without limitation, various file systems, database structures, and/or the like.

The memory 1150 of the interrogator device 140 also can comprise software elements (not shown), including an operating system, device drivers, executable libraries, and/or other code, such as one or more application programs, which may comprise computer programs provided by various embodiments, and/or may be designed to implement methods, and/or configure systems, provided by other embodiments, as described herein. For example, one or more procedures described with respect to the functionality discussed above might be implemented as computer code and/or instructions executable by the interrogator device 140 (and/or processing unit(s) 1110 of the interrogator device 140). The memory 1150 may therefore comprise non-transitory machine-readable media having the instructions and/or computer code embedded therein/thereon.

FIG. 12 is a simplified block diagram of a medical implant 130, according to an embodiment. The medical implant 130 may comprise a "neurograin" or other wireless device configured to perform one or more of the functions within a medical implant of a biological measurement and stimulation system as described in embodiments herein. FIG. 12 is meant only to provide a generalized illustration of various components, any or all of which may be included or omitted as appropriate. It can be further noted that the medical implant 130 may be configured to take measurements and/or stimulate a body part as directed by an interrogator device 140 using communications such as those described in the embodiments herein. A person of ordinary skill in the art will understand that, for the sake of simplicity, some components (e.g., power source, physical housing, etc.) are not shown. It will be understood that, in most embodiments, hardware and/or software optimizations may be made to help minimize power consumption.

The medical implant 130 is shown comprising hardware elements that can be electrically coupled via a bus 1205, or may otherwise be in communication, as appropriate. The hardware elements may include a processing unit(s) 1210 which may comprise without limitation one or more general-purpose processors, one or more special-purpose processors, and/or other logic, processing structure, or means, which can be configured to perform one or more of the methods described herein. The processing unit(s) 1210, may further include one or more counters (implemented in hardware and/or software) as described herein.

The medical implant 130 may further include and/or be in communication with a memory 1220. As with other components of the medical implant 130, the memory 1220 may be optimized for minimum power consumption. In some embodiments, the memory 1220 may be Incorporated into the processing unit(s) 1210. Depending on desired functionality, the memory (which can include a non-transitory computer-readable medium, such as a magnetic, optical, or solid-state medium) may include computer code and/or instructions executable by the processing unit(s) 1210 to perform one or more functions described in the embodiments herein.

A communication interface 1230 and antenna(s) 1235 can enable the medical implant 130 to wirelessly communicate the interrogator device, as described herein. The antenna(s) 1235 may comprise a coiled or other antenna configured to draw power from communications and/or other signals or fields generated by the interrogator device, powering the medical implant 130. In some embodiments, the medical implant 130 may further include an energy storage medium (e.g., a battery, capacitor, etc.) to store energy captured by the antenna(s) 1235. In some embodiments, the communication interface 1230 and antenna(s) 1235 may be configured to the interrogator device using RF backscatter.

The stimulator(s) 1240 of the medical implant 130 can enable the medical implant 130 to provide stimulation to a body part (e.g., biological tissue) in which the medical implant 130 is implanted. As such, the stimulator(s) 1240 may comprise an electrode, light emitting diode (LED), and/or other component configured to provide electrical, optical, and/or other stimulation. The processing unit(s) 1210 may control the operation of the stimulator(s) 1240, and may therefore control the timing, amplitude, and/or other stimulation provided by the stimulator(s) 1240. Some systems may not utilize stimulation (but may instead, for instance, only monitor certain bodily functions), thus the medical implant may not have stimulators(s) 1240 in such embodiments.

The sensor(s) 1250 may comprise one or more sensors configured to receive input from a body part (e.g., biological tissue), in which the medical implant 130 is implanted. Sensors may therefore be configured to sense electrical impulses, pressure, temperature, light, conductivity/resistivity, and/or other aspects of a body part. As described herein, embodiments may enable medical implant 130 to provide this information, via the communication interface 1230, to an interrogator device. Depending on desired functionality, information received by the sensor(s) 1250 may be encrypted, compressed, and/or otherwise processed before it is transmitted via the communication interface 1230.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

The methods, systems, and devices discussed herein are examples. Various embodiments may omit, substitute, or add various procedures or components as appropriate. For instance, features described with respect to certain embodiments may be combined in various other embodiments. Different aspects and elements of the embodiments may be combined in a similar manner. The various components of the figures provided herein can be embodied in hardware and/or software. Also, technology evolves and, thus, many of the elements are examples that do not limit the scope of the disclosure to those specific examples.

It has proven convenient at times, principally for reasons of common usage, to refer to such signals as bits, information, values, elements, symbols, characters, variables, terms, numbers, numerals, or the like. It should be understood, however, that all of these or similar terms are to be associated with appropriate physical quantities and are merely convenient labels. Unless specifically stated otherwise, as is apparent from the discussion above, it is appreciated that throughout this specification discussions utilizing terms such as "processing," "computing," "calculating," "determining," "ascertaining," "identifying," "associating," "measuring," "performing," or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic, electrical, or magnetic quantities within memories, registers, or other information storage devices, transmission devices, or display devices of the special purpose computer or similar special purpose electronic computing device.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AA, AAB, AABBCCC, etc.

Having described several embodiments, various modifications, alternative constructions, and equivalents may be used without departing from the spirit of the disclosure. For example, the above elements may merely be a component of a larger system, wherein other rules may take precedence over or otherwise modify the application of the invention. Also, a number of steps may be undertaken before, during, or after the above elements are considered. Accordingly, the above description does not limit the scope of the disclosure.

What is claimed is:

1. A method of operating an interrogator device having a plurality of antennas to power a plurality of medical implants, the method comprising:

operating a first group of the plurality of antennas during a first time period by powering a first corresponding group of the plurality of medical implants to a first power state while a second group of the plurality of antennas and a second corresponding group of the plurality of medical implants remain in a second power state, different than the first power state; and operating the second group of the plurality of antennas during a second time period by powering the second corresponding group of the plurality of medical implants to the first power state while the first group of the plurality of antennas and the first corresponding group of the plurality of medical implants remain in the second power state.

2. The method of claim 1, wherein the antennas in the first group of the plurality of antennas are not adjacent to each other.

3. The method of claim 1, wherein the antennas in the first group of the plurality of antennas are adjacent to each other, the method further comprising operating an antenna at a center of the first group of the plurality of antennas with a first current and operating other antennas of the first group of the plurality of antennas with a second current, the second current being smaller than the first current.

4. The method of claim 3, wherein all antennas in the first group of the plurality of antennas produce a field that meets at least a first threshold amplitude at a certain depth.

5. The method of claim 4, wherein the antenna at the center of the first group of the plurality of antennas produces a field that meets at least a second threshold amplitude at the certain depth, the second threshold amplitude being higher than the first threshold amplitude.

6. The method of claim 1, further comprising executing a discovery process to determine which one or more medical implants of the plurality of medical implants receive power during the first time period.

7. An interrogator device comprising:
a plurality of antennas configured to power a plurality of medical implants; and
circuitry communicatively coupled with the plurality of antennas and configured to:
operate a first group of the plurality of antennas during a first time period by powering a first corresponding group of the plurality of medical implants to a first power state while a second group of the plurality of antennas and a second corresponding group of the plurality of medical implants remain in a second power state, different than the first power state; and
operate the second group of the plurality of antennas during a second time period by powering the second corresponding group of the plurality of medical implants to the first power state while the first group of the plurality of antennas and the first corresponding group of the plurality of medical implants remain in the second power state.

8. The interrogator device of claim 7, wherein the antennas in the first group of the plurality of antennas are not adjacent to each other.

9. The interrogator device of claim 7, wherein the antennas in the first group of the plurality of antennas are adjacent to each other, and the circuitry is further configured to operate an antenna at a center of the first group of the plurality of antennas with a first current and operate other antennas of the first group of the plurality of antennas with a second current, the second current being smaller than the first current.

10. The interrogator device of claim 9, wherein all antennas in the first group of the plurality of antennas are configured to produce a field that meets at least a first threshold amplitude at a certain depth.

11. The interrogator device of claim 10, wherein the antenna at the center of the first group of the plurality of antennas is configured to produce a field that meets at least a second threshold amplitude at the certain depth, the second threshold amplitude being higher than the first threshold amplitude.

12. The interrogator device of claim 7, wherein the circuitry is further configured to execute a discovery process to determine which one or more medical implants of the plurality of medical implants receive power during the first time period.

13. An apparatus comprising:
means for operating a first group of a plurality of antennas during a first time period by powering a first corresponding group of a plurality of medical implants to a first power state while a second group of the plurality of antennas and a second corresponding group of the plurality of medical implants remain in a second power state, different than the first power state; and
means for operating the second group of the plurality of antennas during a second time period by powering the second corresponding group of the plurality of medical implants to the first power state while the first group of the plurality of antennas and the first corresponding group of the plurality of medical implants remain in the second power state.

14. The apparatus of claim 13, wherein the means for operating the first group of the plurality of antennas comprise means for selecting the antennas in the first group of the plurality of antennas such that they are not adjacent to each other.

15. The apparatus of claim 13, wherein the means for operating the first group of the plurality of antennas comprise means for selecting the antennas in the first group of the plurality of antennas such that they are adjacent to each other, the apparatus further comprising means for operating an antenna at a center of the first group of the plurality of antennas with a first current and operating other antennas of the first group of the plurality of antennas with a second current, the second current being smaller than the first current.

16. The apparatus of claim 15, wherein the means for operating the first group of the plurality of antennas comprise means for causing all antennas in the first group of the plurality of antennas to produce a field that meets at least a first threshold amplitude at a certain depth.

17. The apparatus of claim 16, wherein the means for operating the first group of the plurality of antennas further comprise means for causing the antenna at the center of the first group of the plurality of antennas to produce a field that meets at least a second threshold amplitude at the certain depth, the second threshold amplitude being higher than the first threshold amplitude.

18. The apparatus of claim 13, further comprising means for executing a discovery process to determine which one or more medical implants of the plurality of medical implants receive power during the first time period.

19. A non-transitory computer-readable medium having instructions embedded thereon for operating an interrogator device having a plurality of antennas to power a plurality of medical implants, the instructions comprising computer code for:

operating a first group of the plurality of antennas during a first time period by powering a first corresponding group of the plurality of medical implants to a first power state while a second group of the plurality of antennas and a second corresponding group of the plurality of medical implants remain in a second power state, different than the first power state; and operating the second group of the plurality of antennas during a second time by powering the second corresponding group of the plurality of medical implants to the first power state while the first group of the plurality of antennas and the first corresponding group of the plurality of medical implants remain in the second power state.

20. The non-transitory computer-readable medium of claim 19, wherein the computer code for operating the first group of the plurality of antennas comprises computer code for selecting the antennas in the first group of the plurality of antennas such that they are not adjacent to each other.

21. The non-transitory computer-readable medium of claim 19, wherein the computer code for operating the first group of the plurality of antennas comprises computer code for selecting the antennas in the first group of the plurality of antennas such that they are adjacent to each other, the instructions further comprising computer code for operating an antenna at a center of the first group of the plurality of antennas with a first current and operating other antennas of the first group of the plurality of antennas with a second current, the second current being smaller than the first current.

22. The non-transitory computer-readable medium of claim 21, wherein the computer code for operating the first group of the plurality of antennas comprises computer code for causing all antennas in the first group of the plurality of antennas to produce a field that meets at least a first threshold amplitude at a certain depth.

23. The non-transitory computer-readable medium of claim 22, wherein the computer code for operating the first group of the plurality of antennas further comprises computer code for causing the antenna at the center of the first group of the plurality of antennas to produce a field that meets at least a second threshold amplitude at the certain depth, the second threshold amplitude being higher than the first threshold amplitude.

24. The non-transitory computer-readable medium of claim 19, wherein the instructions further comprise computer code for executing a discovery process to determine which one or more medical implants of the plurality of medical implants receive power during the first time period.

* * * * *